United States Patent [19]

Chowhan et al.

[11] Patent Number: 5,370,744
[45] Date of Patent: Dec. 6, 1994

[54] PROCESS FOR CLEANING AND DISINFECTING CONTACT LENSES

[75] Inventors: Masood Chowhan, Arlington; Thierry Bilbault, Fort Worth; Ronald P. Quintana, Arlington, all of Tex.

[73] Assignee: Alcon Laboratories, Inc., Fort Worth, Tex.

[21] Appl. No.: 113,142

[22] Filed: Aug. 27, 1993

[51] Int. Cl.$^5$ ............................ B08B 3/00; B08B 7/00
[52] U.S. Cl. ............................................. 134/42; 134/26
[58] Field of Search ................................... 134/26, 42

[56] References Cited

U.S. PATENT DOCUMENTS

| | | | |
|---|---|---|---|
| 4,407,791 | 10/1983 | Stark | 424/80 |
| 4,525,346 | 6/1985 | Stark | 424/80 |
| 4,599,195 | 7/1986 | Schafer et al. | 252/546 |
| 4,609,493 | 9/1986 | Schaefer | 252/546 |
| 4,614,549 | 9/1986 | Ogunbiyi et al. | 134/19 |
| 4,731,192 | 3/1988 | Kenjo et al. | 252/95 |
| 4,839,082 | 6/1989 | Bhatia | 134/42 |
| 5,037,647 | 8/1991 | Chowhan et al. | 252/174.23 |

FOREIGN PATENT DOCUMENTS 560506 4/1984 Australia.

OTHER PUBLICATIONS

Houlsby, R., "Microbiological Evaluation of Soft Contact Lens Disinfecting Solutions," *Journal of the American Optometric Association*, vol. 55, No. 3, pp. 205–211 (1984).

Janoff, L., "Origin and Development of Hydrogen Peroxide Disinfection Systems," *The CLAO Journal*, vol. 16, No. 1, (supplement), pp. S36–S42 (1990).

Mandt, et al., "Quantitative Bioburden Determination of Patient Worn Soft Contact Lenses," *Abstracts of the Annual Meeting of the American Society for Microbiology*, Abstract L36, p. 384 (1985).

Minarik, L., et al., "Protein Deposits on Individual Hydrophilic Contact Lenses: Effects of Water and Ionicity," *The CLAO Journal*, vol. 15, No. 3, pp. 185–188 (1989).

Tripathi, R., et al., "Physiochemical Changes in Contact Lenses and Their Interactions with the Cornea and Tears: A Review and Personal Observations," *The CLAO* Journal, vol. 14, No. pp. 23–32 (1988).

Kokai Tokkyo Koho JP 59 45,399 (84 45,399) (Cl. C11D7/26), "Cleansing Solution for Contact Lens," *Chemical Abstracts*, 101:43643h (1984).

Alcon Opti-Free® Rinsing, Disinfecting & Storage Solution, Product Information (package insert).

Bausch & Lomb ReNu® Multi-Purpose Solution, Product Information (package insert).

Primary Examiner—Richard O. Dean
Assistant Examiner—Zeinab El-Arini
Attorney, Agent, or Firm—James A. Arno; Gregg C. Brown

[57] ABSTRACT

An improved process for cleaning and disinfecting contact lenses with a single solution is described. The process utilizes the cleaning effect of a cleaning agent in combination with the solvent action of water and physical agitation of the lens (i.e., by means of rubbing) to achieve a degree of cleaning which is comparable to or better than prior processes which utilize surfactant-cleaners. The cleaning agent is selected from polycarboxylates, polysulfonates and polyphosphates. The preferred cleaning agent is citrate. The process also offers greater convenience, relative to many prior systems for cleaning and disinfecting contact lenses, since the need to utilize additional products to clean the lenses is eliminated.

12 Claims, No Drawings

PROCESS FOR CLEANING AND DISINFECTING CONTACT LENSES

BACKGROUND OF THE INVENTION

The present invention relates to the field of products for treating contact lenses. More particularly, the invention relates to an improved process wherein contact lenses can be cleaned and disinfected with a single product containing one or more polycarboxylates, polysulfonates or polyphosphates. It has been found that these agents effectively remove deposits of proteins and other materials from contact lenses.

Products for treating contact lenses have generally been classified based on the intended use or function of the products. Most products have been classified as either cleaners or disinfectants. However, there are also a number of associated products which can be generally classified as rewetting drops or conditioning solutions. Although there have been attempts to accomplish two or more functions with a single product, such attempts have generally had limited success, because combining the components required to perform multiple functions in a single product tends to reduce the effectiveness of those components. For example, combining surfactants commonly used to clean contact lenses with antimicrobial agents commonly used to disinfect contact lenses may reduce the activity of one or both of these agents. Thus, from a purely scientific standpoint, the combining of two or more functions in a single product has been discouraged.

The perspective of the patient is much different from that of the scientist. The primary concerns of the patient are typically effectiveness and convenience. The latter concern is particularly important among wearers of disposable contact lenses, who tend to be highly motivated toward convenience. The emphasis that patients place on convenience has led to a rapid rise in the popularity of disposable contact lenses capable of supporting either daily or extended wear. Depending on the planned replacement and wearing schedules, these lenses are most commonly cleaned and disinfected daily, and occasionally weekly or biweekly. The result is that many convenience-driven patients who originally sought relief from the rigors of lens care are being fitted with lenses that require daily, albeit less rigorous, care. Such patients place a premium on products that are simple and straightforward to use. By their very nature, frequent replacement lenses worn for daily wear are presumed to require the use of fewer or milder cleaning products. Thus, both patient preference for convenience and the fitting of frequent replacement lenses for daily wear has created a desire for easy-to-use disinfectants that can also be used to clean, soak and rinse lenses.

If the care of the patients' contact lenses becomes too complicated, the patients may fail to comply with the cleaning and disinfection instructions provided by their physicians. Such non-compliance is a major concern of ophthalmologists and optometrists. Repeated failures to clean and/or disinfect contact lenses properly can lead to serious vision problems, such as corneal abrasions, infections, inflammation of the conjunctiva, and so on.

The use of a disinfecting solution to also clean contact lenses has been proposed previously. However, such disinfecting solutions have typically included one or more surfactants as the active cleaning component. A product of this type is currently marketed by Bausch & Lomb as ReNu ® Multi-Purpose Solution.

In view of the foregoing circumstances, there is a need for improved products and processes for cleaning and disinfecting contact lenses in an efficacious but convenient manner.

SUMMARY OF THE INVENTION

The present invention is based on the surprising finding that a single aqueous solution containing a disinfecting agent and a cleaning agent selected from polycarboxylates, polysulfonates and polyphosphates can be effectively utilized to both clean and disinfect contact lenses, provided that this solution is utilized in accordance with the process described herein. That process includes the critical steps of: rubbing a small amount of the solution on both surfaces of the lens, rinsing the lens with the solution, and then soaking the lens in the solution for a time sufficient to achieve disinfection.

The ability to clean contact lenses effectively by means of this process is surprising, since prior products for cleaning contact lenses have typically contained one or more surfactants. The solution utilized in the process of the present invention does not contain a surfactant. It has been discovered that a surfactant is not necessary to achieve a significant degree of cleaning on mildly deposited lenses. More specifically, it has been discovered that a solution which contains polycarboxylates (e.g., citrate), polysulfonates and/or polyphosphates, but no surfactant, achieves a significant degree of cleaning when utilized in accordance with the process of the present invention.

The use of citrate as a component of various types of cleaning products is known. For example, it has been used as a builder in laundry and dishwashing detergents, wherein it has generally been combined with surfactants to achieve cleaning. It has also been utilized in denture cleansers, dentifrices and mouthwashes. The use of citrate in solutions for disinfecting contact lenses is described in U.S. Pat. No. 5,037,647. However, that patent describes the use of citrate as a complexing agent, so as to prevent binding between the above-described polymeric quaternary ammonium compounds and contact lenses. It does not describe the use of citrate as a cleaning agent in a process of the type described and claimed herein. A rinsing, disinfecting and storage solution for contact lenses known as Opti-Free ® (marketed by Alcon Laboratories, Inc.) contains a citric acid/sodium citrate buffer system, but this product has not been utilized in a process for cleaning and disinfecting contact lenses. Similarly, the following patent publications mention citric acid and/or salts thereof as possible components of products for treating contact lenses, but do not disclose the use of these substances in conjunction with a process for cleaning and disinfecting contact lenses with a single, surfactant-free solution: Japanese Patent Publication No. JP 59 45,399 (Kokai Tokkyo Koho); French Patent No. 2,544,880; and U.S. Pat. Nos. 4,599,195; 4,609,493; and 4,614,549.

Citrate is believed to enhance the removal of protein and other deposits through complexation/solubilization actions. More specifically, citrates are known to complex with some biological molecules and to render them more water soluble because of such association. For example, the interaction of citrate with cationic organic molecules is well documented; this includes lysozyme, which is cationic at physiological pH values. Citrate has also been shown to have the ability to displace lysozyme bound by polymers. In terms of cleaning soft contact lenses, citrate is believed to counteract the binding of lysozyme by the lens, rendering the protein more soluble in the aqueous media of the cleaning solution via complexes (i.e., ion pairs) or salt formation, thereby facilitating its removal from the lens when rubbed and rinsed. Additional removal of lysozyme may also take place during the time when lenses are subsequently soaked in the solution during the disinfection stage of the process.

Calcium is another common component of soft lens deposits, occurring as inorganic salts and/or as an element of mixed deposits. In the latter instance, calcium ions can act as a "cross bridge" through ionic bonding and link protein, lipid or mucus-type soilants as well as microbial cells contaminating the surface. While chelation of calcium by citrate effects removal of discrete inorganic deposits, it is believed that it may also have an impact on mixed deposits by disrupting intermolecular bridging, thereby weakening the structural integrity of the deposits and making them more susceptible to the shearing/dispersing/solubilizing effects of rubbing the solution on the lenses.

The cleaning effect achieved with the above-described solutions is accomplished by combining: (1) the mechanical effect of rubbing the soiled lenses with a small amount of the above-described cleaning and disinfecting solution, (2) the solvent action of the water contained in the solution, and (3) the above-described chemical cleaning mechanisms of citrate or the other polycarboxylates, polysulfonates and polyphosphates described herein.

DESCRIPTION OF PREFERRED EMBODIMENTS

The improved contact lens cleaning and disinfecting process of the present invention utilizes an aqueous solution which contains an antimicrobial agent and a cleaning agent selected from polycarboxylates, polysulfonates and polyphosphates. Although various antimicrobial agents may be utilized in the process of the present invention, the preferred antimicrobial agent is a polymeric quaternary ammonium agent known as "polyquaternium-1". This antimicrobial agent is also known as "Onamer M ®" (registered trademark of Millmaster Onyx Group) and "Polyquad ®" (registered trademark of Alcon Laboratories, Inc.). The use of this antimicrobial agent to disinfect contact lenses is described in U.S. Pat. Nos. 4,407,791; 4,525,346; and 5,037,647. The entire contents of the above-cited patents are hereby incorporated in the present specification by reference.

The solutions utilized in the present invention will contain one or more antimicrobial agents in an amount effective to eliminate or substantially reduce the number of viable microorganisms present on the contact lenses being treated, in accordance with criteria established by the United States Food and Drug Administration and corresponding health authorities in other countries. Such an amount is referred to herein as "an amount effective to disinfect". The amount of antimicrobial agent required for this purpose may vary depending on the relative activity of the particular antimicrobial agent selected and other factors familiar to those skilled in the art, such as the tonicity of the solution. The preferred polymeric quaternary ammonium compounds described above are utilized in concentrations of from about 0.00001 to about 3.0 percent by weight, based on the total volume of the solution ("w/v"), preferably from about 0.0001 to 0.1 w/v %.

The solutions utilized in the process of the present invention contain a cleaning agent selected from: (1) polycarboxylates, polysulfonates and polyphosphates; (2) acids corresponding to these salts; and (3) combinations thereof, in an amount effective to facilitate the removal of proteins, calcium and other materials from contact lenses. As utilized herein, the prefix "poly-" means that the molecule contains more than one acid/salt group. The polycarboxylates, polysulfonates and polyphosphates which may be utilized in the present invention include, for example, citrate, succinate, tartrate, malonate, maleate, ethanol diglycinate, diethanol glycinate, polystyerene sulfonate and hexametaphosphate, and other such compounds having a molecular weight of approximately 90 to 600. As utilized herein, the terms "polycarboxylates", "polysulfonates" and "polyphosphates" include both the acid and salt forms of these compounds, as well as mixtures thereof. Similarly, terms such as "citrate", "succinate", and so on, include both the acid and salt form of the compound, as well as mixtures thereof. The sodium, potassium and ammonium salts are preferred. The most preferred polycarboxylate is citrate.

The above-described polycarboxylates, polysulfonates and polyphosphates are utilized in an amount effective to clean the lens. This amount will generally be a molar concentration ranging from 0.013 to 0.13 moles/liter for the salt forms of the compounds, and a molar concentration equivalent to that range for the acid forms of the compounds. The use of a concentration in this range is believed to be necessary in order to achieve cleaning of contact lenses, as described herein.

The cleaning and disinfecting process of the present invention includes three basic steps: cleaning the lenses by means of rubbing a small amount (e.g., one to four drops) of a surfactant-free, aqueous solution containing a disinfecting amount of an antimicrobial agent and one or more of the above-described cleaning agents over the surfaces of the lenses for at least 10 seconds, rinsing the lenses thoroughly to remove all debris, and soaking the lenses in an amount of the same solution sufficient to completely cover the lenses for a period of from at least four hours to overnight. The lenses are preferably allowed to soak in a closed container, such as a contact lens case, and are also preferably rinsed before being replaced in the eye. The above-described process should be repeated on a daily basis.

The present invention is further illustrated by means of the following examples, which are presented for purposes of illustration only and should not be deemed to be limiting in any way.

EXAMPLE 1

The following formulation is the preferred surfactant-free cleaning and disinfecting solution for use in the process of the present invention.

|  | w/v % |
| --- | --- |
| Polyquad ® | 0.001 + 10% excess |
| Sodium Chloride | 0.52 |
| Disodium edetate | 0.05 |
| Citric acid monohydrate | 0.021 |
| Sodium citrate dihydrate | 0.56 |
| Purified Water | q.s. |

This solution may be prepared as follows. The purified water, sodium citrate dihydrate, citric acid monohydrate, disodium edetate, sodium chloride and Polyquad ® are combined and then dissolved by stirring with a mixer. Additional purified water is then added to bring the solution to 100%. The pH is then adjusted (if necessary) to pH 7.0.

The following examples demonstrate the cleaning effect of the citrate-containing formulations utilized in the present invention.

EXAMPLE 2

An in vitro study was conducted to determine the cleaning effect of the solution described in Example 1 above (i.e., Opti-Free ® Rinsing, Disinfecting and Storage Solution) on lenses from the four FDA soft lens polymer groupings. The study compared the solution's cleaning ability to that of Bausch & Lomb's ReNu ® Multi-Purpose Solution on heavily deposited soft contact lenses. ReNu ® Multi-Purpose Solution (sometimes referred to herein as "ReNu ®-MPS") is a sterile, isotonic solution that contains boric acid, edetate disodium, poloxamine, sodium borate and sodium chloride; it is preserved with DYMED (polyaminopropyl biguanide) 0.00005%.

New (i.e., unworn) contact lenses of the following types were utilized in the study:

| Lens Group* | Lens Name | Manufacturer | Polymer | Water Content |
|---|---|---|---|---|
| I | Soflens | Bausch & Lomb | Polymacon | 38% |
| II | B&L 70 | Bausch & Lomb | Lidofilcon A | 70 |
|  | Permaflex | CooperVision | Surfilcon A | 74 |
| III | Durasoft 2 | Wesley-Jessen | Phemfilcon A | 38 |
|  | Hydrocurve II | SBH | Bufilcon A | 45 |
| IV | Durasoft 3 | Wesley-Jessen | Phemfilcon A | 55 |

*Group I = Low-water-content, nonionic polymers
Group II = High-water-content, nonionic polymers
Group III = Low-water-content, ionic polymers
Group IV = High-water-content, ionic polymers The lenses were deposited with an artificial tear solution prepared to mimic common lens deposits. This artificial tear solution was prepared by dissolving sodium phosphate and sodium biphosphate in a beaker containing 90% of volume of purified water, USP. Dissolution was achieved by stirring on a magnetic stir plate with a magnetic stir bar for 10–15 minutes. Lysozyme in an amount to equal 0.05% final concentration by weight was added and allowed to dissolve, following which the solution was brought to 100% volume with purified water, USP. The pH of the solution was approximately 7.4 with no adjustment.

The test lenses were rinsed with sterile 0.9% sodium chloride solution and blotted dry with lint-free towels, after which the lenses were placed in clean glass vials. Five milliliters (mL) of the artificial tear solution was added to each vial. The vials were stoppered and clamped and placed in a preheated water bath and heated at 90° C. for 15 minutes. Following the water bath treatment, the vials were removed and allowed to cool to room temperature. The lenses were then removed from the vials, rubbed, and rinsed with 0.9% sodium chloride solution remove loosely bound protein. The lenses were placed in clean glass vials with 5 mL of OPTI-PURE ® sterile saline and stoppered.

The test procedure consisted of an initial rating of the in vitro deposited lenses by two trained raters following the FDA recommended Rudko method. After initial rating the lenses were transferred to a third person who performed cleaning by following a procedure similar to that which is normally recommended for the daily cleaning of human worn lenses: The lenses were placed in the palm of the hand and two drops of cleaning solution from the coded bottles were applied to each lens surface. The lenses were then gently rubbed for 40 seconds and subsequently rinsed thoroughly with the test solution. Deposited Group IV lenses were put through three cleaning cycles for both solutions since neither produced significant cleaning with this group of lenses after just one cycle of cleaning. The lens deposits were then rated again using the Rudko method by the two raters not involved in the cleaning steps.

The in vitro deposited lenses were rated before and after rubbing and rinsing by two technicians who were masked with respect to solutions used. The ratings were converted into numerical scores. The numerical scores for all lenses in a set were then added to obtain a cumulative score, and that score was divided by the number of lenses in that set to obtain an average score for a lens in that set. The overall cleaning efficacy of each solution was computed as a percentage utilizing the average rating of cleaned lenses and that of deposited lenses prior to cleaning. The results are presented below:

Composite of Comparative Cleaning Efficacy of Opti-Free ® Rinsing, Disinfecting and Storage Solution and ReNu ® Multi-Purpose Solution Using Converted Rudko Numerical Scores

| Product | Group I* Soflens | | |
|---|---|---|---|
| Opti-Free ® | 60 | | |
| ReNu ® | 36 | | |

| Product | Group II B&L 70 | Permaflex | Composite |
|---|---|---|---|
| Opti-Free ® | 10 | 86 | 48 |
| ReNu ® | 8 | 65 | 36 |

| Product | Group III Durasoft 2 | Hydrocurve II | Composite |
|---|---|---|---|
| Opti-Free ® | 39 | 54 | 46 |
| ReNu ® | 77 | 45 | 61 |

| Product | Group IV Durasoft 3 Cycle 1 | Cycle 2 | Cycle 3 |
|---|---|---|---|
| Opti-Free ® | 3 | 11 | 53 |
| ReNu ® | 6 | 19 | 64 |

*NOTE:
In a prior study with Group I lenses using the same procedures as those described herein, the composite cleaning scores for Opti-Free ® and ReNu ® were 58 and 90, respectively. The average cleaning of the Group I lenses based on these two studies is therefore 59 (Opti-Free ®) and 63 (ReNu ®).

The foregoing results show that both the solution of Example 1 and ReNu ® Multi-Purpose Solution removed a substantial amount of protein from in vitro deposited soft contact lenses. The cleaning efficacy of these two solutions was found to be dependent on the lens brand for Groups II and III. Overall, the cleaning efficacy of the two products in this study was comparable.

EXAMPLE 3

A study was conducted to evaluate the role of citrate in cleaning Group IV contact lenses (i.e., Durasoft 3). This study compared the cleaning effect of the solution described in Example 1 above (i.e., Opti-Free ® Rinsing, Disinfecting and Storage Solution) with modified versions of that solution, and with ReNu ® Multi-Purpose Solution. The composition of the solutions utilized in the study is presented in the following table:

TABLE 1

Comparative Compositions of Test Solutions*
% w/v in Solutions

| Ingredients | 92-2545 | 92-2600 | 92-2601 | 92-2603 | Opti-Free ® |
|---|---|---|---|---|---|
| Citric Acid Monohydrate, USP | 0.021 | None | None | None | 0.021 |
| Sodium Citrate, USP | 0.56 | None | None | None | 0.56 |
| Disodium EDTA (Edetate Disodium), USP | 0.05 | 0.05 | 0.05 | 0.05 | 0.05 |
| Sodium Chloride, USP | 0.48 | 0.48 | 0.48 | None | 0.48 |
| Mannitol, USP | None | None | 1.0 | None | None |
| Polyquad, NOC | None | None | None | None | 0.001 (+10% excess) |
| Sodium Hydroxide, NF and/or Hydrochloric Acid, NF | q.s. to adjust pH to 7.0 | q.s. to adjust pH to 7.0 | q.s. to adjust pH to 7.0 | q.s. to adjust pH to 7.0 | q.s. to adjust pH to 7.0 |
| Purified Water, USP | q.s. 100 | q.s. 100 | q.s. 100 | q.s. 100 | q.s. 100 |

The test procedures used in the study are described below.

I. Preparation of Deposition Solution

A. Phosphate Buffered Saline ("PBS")

1.311 g of sodium phosphate (monobasic, monohydrate), 5.749 g sodium phosphate (dibasic, anhydrous), and 0.9 g sodium chloride were dissolved in distilled water and the solution was brought to volume (1000 mL) with distilled water. The final concentration of each component in the solution was: sodium phosphate, 0.05M; sodium chloride, 0.14M. The final pH was 7.4 (drops of 5N NaOH or phosphoric acid may be added if pH adjustment is needed).

B. Dansyl-lysozyme Solution 750 mg of dansyl-lysozyme was dissolved in 500 mL phosphate buffered saline. The final concentration of dansyl-lysozyme was 1.5 mg/mL.

II. Lens Deposition Procedure

Each lens was immersed in a Wheaton glass vial (8 mL capacity) containing 5 mL of dansyl-lysozyme solution (1.5 mg/mL in PBS). The vials were closed with a plastic snap cap and incubated in a constant temperature water bath at 37° C. for 24 hours. After incubation, each deposited lens was rinsed by dipping into three (3) consecutive beakers containing 50 mL of distilled water to remove any excess of deposition solution and loosely bound dansyl-lysozyme, and blotted gently with a laboratory towel (KayPees). These lenses served as the soiled lenses for total protein determination (control lenses) as well as for the evaluation of cleaning efficacies.

III. Protein Determination on Control Lenses

Five (5) deposited lenses were used as control lenses to determine the total dansyl-lysozyme deposition on the lenses. For this purpose, each deposited lens was extracted with 10 mL SDS extraction solution (0.1M Tris-HCl, pH 8.0, containing 2% SDS, 0.1% Dithiothreitol, and 0.1 mM EDTA) in a screw-capped glass scintillation vial (20 mL capacity). The extraction was conducted by shaking the vial with a rotary shaker (Red Rotor) at room temperature for at least 48 hours. The amount of dansyl-lysozyme extracted from each lens was assessed by fluorescence measurement with a fluorospectrophotometer. The total protein was calculated based on the standard curve established for dansyl-lysozyme solution.

IV. Cleaning Procedure

Lenses were placed in Wheaton glass vials (12 mL capacity) containing 5 mL of test solution, with five (5) lenses being used for each test solution. The vials were capped with plastic snap caps and gently agitated on a rotary shaker at room temperature for six (6) or twenty-four (24) hours. The lenses were removed from their respective test solutions after soaking and were rinsed with distilled water as described previously under "Lens Deposition Procedure." The lenses were then subjected to an extraction procedure as described under "Protein Determination on Control Lenses." Both the test soaking solutions and the lens extraction solution were subjected to fluorescence measurements for protein determination.

V. Protein Determination

Quantitative determination of protein for the soaking solutions and the lens extracts were carried out by use of a fluorospectrophotometer. Two (2) mL of solution were required for each measurement. The fluorescence intensity was measured by setting the excitation/emission wavelength at 252 nm/530 nm with excitation/emission slits of 2.0 nm/8.5 nm. Dansyl-lysozyme concentrations for each solution and extract were calculated based on the slope established from linear standard dansyl-lysozyme curves developed under the identical instrumental conditions for SDS-extraction buffer and phosphate buffered saline respectively.

The following table shows a summary of the cleaning results for the six (6) and twenty-four (24) hours soaking for each test solution.

TABLE 2

Dansyl-Lysozyme Removed (μg/lens ± SD) by Evaluated Solutions

| Time | 92-2545 | 92-2600 | 92-2601 | 92-2603 | Opti-Free ® | ReNu ®-MPS |
|---|---|---|---|---|---|---|
| 6 Hours | 65.08 ± 1.66 | 24.26 ± 0.90 | 23.57 ± 1.25 | 24.30 ± 1.60 | 71.83 ± 2.15 | 36.79 ± 2.53 |
| 24 Hours | 87.67 ± | 28.01 ± | 28.64 ± | 37.92 ± | 100.92 ± | 44.53 ± |

TABLE 2-continued

| | Dansyl-Lysozyme Removed (μg/lens ± SD) by Evaluated Solutions | | | | | |
|---|---|---|---|---|---|---|
| Time | 92-2545 | 92-2600 | 92-2601 | 92-2603 | Opti-Free ® | ReNu ®-MPS |
| | 1.60 | 0.85 | 1.23 | 3.08 | 1.85 | 3.61 |

The results of this study indicate that Opti-Free ® and Solution 92-2545, both containing citrate, removed more dansyl-lysozyme from lenses than Solutions 92-2603, 92-2600, and 92-2601, all of which contained no citrate. The differences were significant based upon statistical analysis ($p < 0.05$). Opti-Free ® and Solution 92-2545 (Opti-Free ® minus Polyquad ®) also removed more dansyl-lysozyme from the deposited lenses than did ReNu ® Multi-Purpose Solution, evaluated under the same experimental conditions. These results were also statistically significant ($p < 0.05$).

The cleaning results observed during a prior experiment involving the same solutions and procedures were substantially similar to the results presented above. The results observed during the prior experiment are presented in the following table:

TABLE 3

| | Dansyl-Lysozyme Removed (μg/lens ± SD) by Evaluated Solutions | | | | | |
|---|---|---|---|---|---|---|
| Time | 92-2545 | 92-2600 | 92-2601 | 92-2603 | Opti-Free ® | ReNu ®-MPS |
| 6 Hours | 68.36 ± 1.72 | 26.62 ± 1.15 | 27.98 ± 1.59 | 28.46 ± 1.61 | 72.68 ± 1.83 | 43.10 ± 1.37 |
| 24 Hours | 82.28 ± 7.87 | 36.16 ± 1.55 | 34.00 ± 1.12 | 47.32 ± 1.28 | 92.12 ± 3.71 | 45.00 ± 0.88 |

EXAMPLE 4

Another study similar to the study described in Example 3 above, but which involved somewhat different procedures, was also conducted to further evaluate the role of citrate in cleaning Group IV contact lenses (i.e., Durasoft 3). The study evaluated the cleaning effect of four of the same solutions tested in Example 3 (i.e., 92-2545; 92-2600; 92-2601; and 92-2603). The procedures used in this study are described below.

I. Preparation of Deposition Solution

A. Composition

| Ingredients | % w/v |
|---|---|
| Lysozyme | 0.15 |
| Sodium Phosphate, Basic | 0.689 |
| Sodium Chloride | 0.9 |
| Sodium Hydroxide, 5N | q.s. pH 7.4 |
| Purified Water | q.s. 100 |

B. Procedure

Sodium chloride was dissolved in a beaker containing 80% of the total required volume of purified water. Sodium phosphate was added and dissolved while stirring. Lysozyme was then added and allowed to dissolve. The pH of the solution was adjusted to 7.4 with sodium hydroxide, and the volume of the solution was adjusted with water.

II. Experimental Procedure

A. Study Design

Lenses were numbered from one to ninety. After deposition, ten lenses were not cleaned and used as control lenses to determine average lysozyme uptake per lens. The remaining eighty lenses were divided into four groups of twenty lenses and each group was cleaned with the respective test solutions. Ten cleaning solution samples from each group were pulled for analysis after six hours and the remaining ten from each group after 24 hours.

B. Lens Deposition Procedure

Each lens was immersed in a glass vial containing 5 mL of the deposition solution. Vials containing the deposition solution and lenses were incubated for 24 hours at 37° C. Each deposited lens was rinsed by dipping into three (3) consecutive beakers containing 50 mL of purified water to remove any excess of deposition solution and loosely bound protein.

C. Control

Ten deposited lenses were used as control lenses to determine lysozyme deposition on the lenses. After rinsing as described above these were gently blotted to remove any excess water and placed into screw cap glass culture tubes. The tubes were stored in the freezer until analysis. Additionally, five (5) new lenses were included to provide non-deposited lens values for the ninhydrin procedure described below.

D. Cleaning Procedure

Six Hour Samples

Ten lenses per test solution were gently blotted to remove excess water following rinsing. The lenses were placed in plastic vials containing 5 mL of test solution. The vials and their contents were gently agitated for six (6) hours. The lenses were removed from their respective test solutions after cleaning and the solutions refrigerated until analyzed.

Twenty-four Hour Samples

Ten lenses per test solution were gently blotted to remove excess water following rinsing. The lenses were placed in plastic vials containing 5 mL of test solution. The vials and their contents were gently agitated for twenty-four (24) hours. The lenses were removed from their respective test solutions after cleaning and the 24 hour cleaning solutions along with the control lenses and six hour cleaning solutions were assayed for protein using the ninhydrin procedure.

E. Protein Analysis of Solutions and Control Lenses

The samples were evaluated by means of a ninhydrin assay procedure. In this procedure, proteins are hydrolyzed under alkaline conditions to their amino acid components which react with ninhydrin to form a colored complex. The latter can be quantitated by measuring absorbance at 570 nm. For this study a standard curve was prepared covering a range of 5.00 to 15.00 μg lysozyme. The curve had a slope of 0.050 AU/μg, a y intercept of 0.021 AU and a R-squared value of 0.9811. The quantity of protein in a sample was determined using this standard curve and multiplying by appropriate dilution factors.

The following table shows a summary of the cleaning data for the six (6) and twenty-four (24) hours cleaning:

| Lysozyme Removed (μg/lens) by Evaluated Solutions | | | | |
|---|---|---|---|---|
| | 92-2545 | 92-2600 | 92-2601 | 92-2603 |
| 6 Hours | 47.52 | −6.40 | 15.02 | 2.20 |
| 24 Hours | 52.92 | −2.33 | −11.08 | 19.62 |

This study shows that significantly ($p<0.05$) more lysozyme is cleaned from lenses when citrate is present than when it is absent. Thus, the results demonstrate that citrate has cleaning properties that are effective in removing lysozyme from contact lenses.

In another cleaning study, which used a HPLC assay procedure instead of the above-described ninhydrin method, similar results were obtained, as shown in the following table:

| Lysozyme Removed (μg/lens) by Evaluated Solutions | | | | |
|---|---|---|---|---|
| | 92-2545 | 92-2600 | 92-2601 | 92-2603 |
| 6 Hours | 39.0 | 6.6 | 6.2 | 3.7 |
| 24 Hours | 95.3 | 10.6 | 7.7 | 5.5 |

While there is not absolute agreement between these two studies (in part due to substraction of large blank value and the lesser precision associated with the ninhydrin assay) with all solutions, both studies clearly show that the 92-2545 solutions contain significantly higher levels of lysozyme than the others. Thus, the importance of citrate in removing protein deposits is demonstrated by these studies.

What is claimed is:

1. A process for cleaning and disinfecting a contact lens with a single solution which comprises:
   rubbing a small amount of the solution over the surface of the lens;
   rinsing the lens to remove debris loosened by said rubbing; and
   soaking the lens in the solution for a time sufficient to disinfect the lens;
   wherein the solution is surfactant-free and comprises:
   an ophthalmically acceptable antimicrobial agent in an amount effective to disinfect the lens; a cleaning agent selected from the group consisting of polycarboxylates, polysulfonates and polyphosphates having a molecular weight of 90 to 600, in an amount effective to clean the lens; and an aqueous vehicle therefor.

2. A process according to claim 1, wherein the lens is rubbed with the solution for at least 10 seconds, and the rubbing is performed by placing the lens in the palm of one hand, applying approximately one to four drops of the solution to the lens, and then rubbing the solution over both surfaces of the lens with a finger of the other hand.

3. A process according to claim 1, wherein the lens is soaked in the solution for at least four hours.

4. A process according to claim 1, wherein the cleaning agent is selected from the group consisting of citrate, succinate, tartrate, malonate, maleate, ethanol diglycinate, diethanol glycinate, polystyrene sulfonate and hexametaphosphate.

5. A process according to claim 1, wherein the cleaning agent comprises citrate.

6. A process according to claim 5, wherein the antimicrobial agent comprises polyquaternium-1.

7. A process for removing protein deposits from a contact lens which comprises:
   rubbing a small amount of a cleaning solution over the surface of the lens;
   rinsing the lens to remove debris loosened by said rubbing; and soaking the lens in the cleaning solution;
   wherein the cleaning solution comprises: a cleaning agent consisting essentially of a compound selected from the group consisting of polycarboxylates, polysulfonates and polyphosphates having a molecular weight of 90 to 600, in an amount effective to clean the lens; and an aqueous vehicle therefor.

8. A process according to claim 7, wherein the lens is rubbed with the cleaning solution for at least 10 seconds, and the rubbing is performed by placing the lens in the palm of one hand, applying approximately one to four drops of the cleaning solution to the lens, and then rubbing the cleaning solution over both surfaces of the lens with a finger of the other hand.

9. A process according to claim 7, wherein the lens is soaked in the cleaning solution for at least four hours.

10. A process according to claim 7, wherein the compound is selected from the group consisting of citrate, succinate, tartrate, malonate, maleate, ethanol diglycinate, diethanol glycinate, polystyrene sulfonate and hexametaphosphate.

11. A process according to claim 10, wherein the compound comprises citrate.

12. A process according to claim 7, wherein the cleaning solution is surfactant-free.

* * * * *

REEXAMINATION CERTIFICATE (3926th)

United States Patent [19]
Chowhan et al.

[11] B1 5,370,744
[45] Certificate Issued Nov. 9, 1999

[54] PROCESS FOR CLEANING AND DISINFECTING CONTACT LENSES

[75] Inventors: Masood Chowhan, Arlington; Thierry Bilbault, Fort Worth; Ronald P. Quintana, Arlington, all of Tex.

[73] Assignee: Alcon Laboratories, Inc., Fort Worth, Tex.

Reexamination Request:
No. 90/005,299, Mar. 11, 1999

Reexamination Certificate for:
Patent No.: 5,370,744
Issued: Dec. 6, 1994
Appl. No.: 08/113,142
Filed: Aug. 27, 1993

[51] Int. Cl.$^6$ ............................. B08B 3/00; B08B 7/00
[52] U.S. Cl. ................................. 134/42; 134/26
[58] Field of Search ....................... 134/26, 42

[56] References Cited

U.S. PATENT DOCUMENTS

| | | | |
|---|---|---|---|
| 3,882,036 | 5/1975 | Krezanoski et al. | 252/106 |
| 4,323,467 | 4/1982 | Fu | 252/106 |
| 4,395,346 | 7/1983 | Kleist | 252/135 |
| 4,537,746 | 8/1985 | Ogunbiyi et al. | 422/28 |
| 4,642,234 | 2/1987 | Davies et al. | 424/78 |
| 4,734,222 | 3/1988 | Winterton et al. | 252/546 |
| 4,820,352 | 4/1989 | Riedhammer et al. | 134/30 |
| 4,863,627 | 9/1989 | Davies et al. | 252/95 |
| 4,889,689 | 12/1989 | Tsao | 422/30 |
| 5,000,867 | 3/1991 | Heinhuis-Walther et al. | 252/106 |
| 5,037,647 | 8/1991 | Chowhan et al. | 424/78 |
| 5,576,028 | 11/1996 | Martin et al. | 424/613 |

FOREIGN PATENT DOCUMENTS

| | | | |
|---|---|---|---|
| 2 098 472 | 12/1993 | Canada | A01N 47/44 |
| 0 456 467 A2 | 11/1991 | European Pat. Off. | A61L 2/00 |
| 0 384 666 B1 | 11/1994 | European Pat. Off. | A61L 2/18 |
| 57-48712 | 3/1982 | Japan | G02C 13/00 |
| 57-116319 | 7/1982 | Japan | A61L 2/18 |
| 59-045399 | 3/1984 | Japan | C11D 7/26 |
| 62-153217 | 7/1987 | Japan | A61K 31/14 |
| 1-099022 | 4/1989 | Japan . | |
| WO 91/17469 | 11/1991 | WIPO | G02C 13/00 |

OTHER PUBLICATIONS

H. Hamano, "How To Wash Hard Lenses", *Contact Lens*, Fujin Gaho Co., pp. 70 and 77 (Feb. 15, 1983).

"International Search Report" for International Application No. PCT/US94/09521.

"Information Offer Form" filed by Tome Technology K.K. on May 20, 1998 in connection with Japanese Patent Application No. 7–507732, which corresponds to U.S. Patent No. 5,370,744.

"Dequest Phosphonates by Monsanto, An Introductory Guide" (Publication No. 745 9151A) (1994).

American Chemical Society Registry (Registry No. 3794–83–0) (1997).

*Primary Examiner*—Zeinab El-Arini

[57] ABSTRACT

An improved process for cleaning and disinfecting contact lenses with a single solution is described. The process utilizes the cleaning effect of a cleaning agent in combination with the solvent action of water and physical agitation of the lens (i.e., by means of rubbing) to achieve a degree of cleaning which is comparable to or better than prior processes which utilize surfactant-cleaners. The cleaning agent is selected from polycarboxylates, polysulfonates and polyphosphates. The preferred cleaning agent is citrate. The process also offers greater convenience, relative to many prior systems for cleaning and disinfecting contact lenses, since the need to utilize additional products to clean the lenses is eliminated.

REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 36–52:

The improved contact lens cleaning and disinfecting process of the present invention utilizes an aqueous solution which contains an antimicrobial agent and a cleaning agent selected from polycarboxylates, polysulfonates and polyphosphates. Although various antimicrobial agents may be utilized in the process of the present invention, the preferred antimicrobial agent is a polymeric quaternary ammonium agent known as "polyquaternium-1". This antimicrobial agent is also known as "Onamer M ®" (registered trademark of Millmaster Onyx Group) and "Polyquad ®" (registered trademark of Alcon Laboratories, Inc.). The use of this antimicrobial agent to disinfect *soft, hydrophilic* contact lenses is described in U.S. Pat. Nos. 4,407,791; 4,525,346; and 5,037,647. The entire contents of the above-cited patents are hereby incorporated in the present specification by reference.

AS A RESULT OF REEXAMINATION, IT HAS BEEN DETERMINED THAT:

Claims 4, 9–10 and 11 are cancelled.

Claims 1–2, 5 and 7–8 are determined to be patentable as amended.

Claims 3, 6 and 12, dependent on an amended claim, are determined to be patentable.

New claims 13–45 are added and determined to be patentable.

1. A process for cleaning and disinfecting a *soft, hydrophilic* contact lens with a single solution, which comprises *performing the following steps on a daily basis*:

rubbing a small amount of the solution over the [surface] *surfaces* of the lens *for at least 10 seconds*:

rinsing the lens *with the solution* to remove *proteins and other* debris lossened by said rubbing; and soaking the lens in the solution *for a time sufficient to facilitate the further removal of protein deposits from the lens and* disinfect the lens;

*wherein the solution is surfactant-free, has a neutral pH,* and comprises:

an ophthalmically acceptable antimicrobial agent in an amount effective to disinfect the lens; a cleaning agent *for removing protein deposits attached to the lens, said cleaning agent consisting essentially of a compound* selected from the group consisting of polycarboxylates, polysulfonates and polyphosphates *having a molecular weight of 90 to 600*, in an amount effective to clean the lens; and an aqueous vehicle therefor.

2. A process according to claim 1, wherein [the lens is rubbed with the solution for at least 10 seconds, and] the rubbing is performed by placing the lens in the palm of one hand, applying approximately one to four drops of the solution to *each of the surfaces of* the lens, and then rubbing the solution over both surfaces of the lens with a finger on the other hand.

5. A process according to claim 1, wherein the cleaning agent [comprises] *consists essentially of* citrate.

7. A process for removing protein deposits from a *soft, hydrophilic* contact lens, which comprises *performing the following steps on a daily basis*:

*applying a small amount of an aqueous cleaning solution to the surface of the lens;* rubbing [a small amount of a] *the* cleaning solution over the [surface] *surfaces* of the lens *for at least 10 seconds*;

rinsing the lens *with the cleaning solution* to remove *proteins and other* debris loosened by said rubbing; and soaking the lens in the cleaning solution *to facilitate the further removal of protein deposits from the lens*;

*wherein the cleaning solution has a neutral pH and* comprises: a cleaning agent *for removing protein deposits attached to the lens, said cleaning agent consisting essentially of a compound selected from the* group consisting of [polycarboxylates,] polysulfonates and polyphosphates *having a molecular weight of 90 to 600*, in an amount effective to clean the lens; and an aqueous vehicle therefor.

8. A process according to claim 7, wherein [the lens is rubbed with the cleaning solution for at least 10 seconds, and the rubbing is] *the applying and rubbing steps are* performed by placing the lens in the palm of one hand, applying approximately one to four drops of the cleaning solution to *each of the surfaces of* the lens, and then rubbing the cleaning solution over both surfaces of the lens with a finger of the other hand.

*13. A process according to claim 8, wherein the cleaning agent for removing protein deposits consists essentially of a polyphosphate.*

*14. A process according to claim 13, wherein the lens is soaked in the cleaning solution for at least four hours.*

*15. A process according to claim 14, wherein said cleaning agent facilitates the removal of protein deposits from the lens by (i) counteracting binding between proteins and the surfaces of the lens, and (ii) disrupting intermolecular bridging within the deposits.*

*16. A process according to claims 7, 8, 12 or 13 to 15, wherein the lens is a frequent replacement lens.*

*17. A process according to any one of claims 7, 8, 12 or 13 to 15, wherein the lens is a Group IV lens.*

*18. A process for removing protein deposits from a soft, hydrophilic contact lens while disinfecting the lens, which comprises performing the following steps on a daily basis:*

*applying a small amount of an aqueous cleaning and disinfecting solution to the surfaces of the lens;*

*rubbing the aqueous cleaning and disinfecting solution over the surfaces of the lens for at least 10 seconds;*

*rinsing the lens with the cleaning and disinfecting solution to remove proteins and other debris loosened by said rubbing; and*

*soaking the lens in the cleaning and disinfecting solution for at least four hours to facilitate the further removal of protein deposits from the lens and disinfect the lens;*

*said cleaning and disinfecting solution having a neutral pH and comprising: a cleaning agent for removing protein deposits attached to the lens, said cleaning* agent consisting essentially of a compound selected from the group consisting of polysulfonates and polyphosphates having a molecular weight of 90 to 600, in an amount effective to clean the lens; an ophthalmically acceptable antimicrobial agent in an amount effective to disinfect the lens; and an aqueous vehicle therefor.

19. A process according to claim 18, wherein the antimicrobial agent comprises polyquaternium-1.

20. A process according to claim 18, wherein the cleaning agent for removing protein deposits consists essentially of a polyphosphate.

21. A process according to claim 20, wherein the antimicrobial agent comprises polyaminopropyl biguanide.

22. A process according to claim 21, wherein said cleaning agent facilitates the removal of protein deposits from the lens by (i) counteracting binding between proteins and the surfaces of the lens, and (ii) disrupting intermolecular bridging within the deposits.

23. A process according to claim 18, wherein the cleaning and disinfecting solution is surfactant-free.

24. A process according to any one of claims 18 to 23, wherein the lens is a frequent replacement lens.

25. A process according to any one of claims 18 to 23, wherein the lens is a Group IV lens.

26. A process for cleaning and disinfecting a soft contact lens having hydrophilic surfaces, said process consisting essentially of the following steps, performed on a daily basis:
  applying a small amount of a single solution to the surfaces of the lens, said single solution having a neutral pH and comprising: a cleaning agent for removing protein deposits attached to the lens, said cleaning agent consisting essentially of a compound selected from the group consisting of polycarboxylates, polysulfonates and polyphosphates having a molecular weight of 90 to 600, in an amount effective to clean the lens; an ophthalmically acceptable antimicrobial agent in an amount effective to disinfect the lens; and an aqueous vehicle therefor;
  rubbing said single solution over the surfaces of the lens for at least 10 seconds;
  rinsing the lens with said single solution to remove proteins and other debris loosened by said rubbing; and
  soaking the lens in said single solution for a time sufficient to facilitate the further removal of protein deposits from the lens and disinfect the lens.

27. A cleaning and disinfecting process according to claim 26, wherein the cleaning agent for removing protein deposits consists essentially of citrate.

28. A cleaning and disinfecting process according to claim 27, wherein the antimicrobial agent comprises polyquaternium-1.

29. A cleaning and disinfecting process according to claim 26, wherein the cleaning agent for removing protein deposits consists essentially of a polyphosphate.

30. A cleaning and disinfecting process according to claim 29, wherein the antimicrobial agent comprises polyaminopropyl biguanide.

31. A cleaning and disinfecting process according to claim 26, wherein said single solution is surfactant-free.

32. A cleaning and disinfecting process according to any one of claims 26 to 31, wherein said cleaning agent facilitates the removal of protein deposits from the lens by (i) counteracting binding between proteins and the surfaces of the lens, and (ii) disrupting intermolecular bridging within the deposits.

33. A cleaning and disinfecting process according to any one of claims 26 to 31, wherein the lens is soaked in said single solution for at least four hours.

34. A cleaning and disinfecting process according to any one of claims 26 to 31, wherein the lens is a frequent replacement lens.

35. A cleaning and disinfecting process according to any one of claims 26 to 31, wherein the lens is a Group IV lens.

36. A process for cleaning and disinfecting a soft contact lens having hydrophilic surfaces, said process consisting essentially of the following steps, performed on a daily basis;
  placing the lens in the palm of one hand;
  applying one to four drops of a single solution to each side of the lens, said single solution having a neutral pH and comprising: a cleaning agent for removing protein deposits attached to the lens, said cleaning agent consisting essentially of a polycarboxylate having a molecular weight of 90 to 600, in an amount effective to clean the lens; an ophthalmically acceptable antimicrobial agent in an amount effective to disinfect the lens, said antimicrobial agent comprising polyquaternium-1; and an aqueous vehicle therefor;
  rubbing said single solution over the surfaces of the lens with a finger of the other hand for at least 10 seconds;
  rinsing the lens with said single solution to remove proteins and other debris loosened by said rubbing; and
  soaking the lens in said single soultion for at least four hours to facilitate the further removal of protein deposits from the lens and disinfect the lens.

37. A cleaning and disinfecting process according to claim 36, wherein said cleaning agent facilitates the removal of protein deposits from the lens by (i) complexing with proteins contained in the deposits, so as to counteract binding between the proteins and the hydrophilic surfaces of the lens and render the proteins nore soluble in the multipurpose solution, and (ii) complexing with calcium contained in mixed deposits of proteins and other materials, so as to disrupt intermolecular bridging within the mixed deposits and weaken the structural integrity of the deposits.

38. A cleaning and disinfecting process according to claim 36, wherein said single solution is surfactant-free.

39. A cleaning and disinfecting process according to any one of claims 36 to 38, wherein the lens is a frequent replacement lens.

40. A cleaning and disinfecting process according to any one of claims 36 to 38, wherein the lens is a Group IV lens.

41. A process for cleaning and disinfecting a soft contact lens having hydrophilic surfaces, said process consisting essentially of the following steps, performed on a daily basis:
  placing the lens in the palm of one hand;
  applying one to four drops of a single solution to each side of the lens, said single solution having a neutral pH and comprising: a cleaning agent for removing protein deposits attached to the lens, said cleaning agent consisting essentially of a polyphosphate having a molecular weight of 90 to 600, in an amount effective to clean the lens; an ophthalmically acceptable antimicrobial agent in an amount effective to disinfect the lens, said antimicrobial agent comprising polyaminopropyl biguanide; and an aqueous vehicle therefor;
  rubbing said single solution over the surfaces of the lens with a finger of the other hand for at least 10 seconds;
  rinsing the lens with said single solution to remove proteins and other debris loosened by said rubbing; and soaking the lens in said single solution for at least four hours to facilitate further removal of protein deposits from the lens and disinfect the lens.

42. A cleaning and disinfecting process according to claim 41, wherein said cleaning agent facilitates the removal of protein deposits from the lens by (i) complexing with proteins containing in the deposits, so as to counteract binding between the proteins and the hydrophilic surfaces of the lens and render the protein more soluble in the multi-purpose solution, and (ii) complexing with calcium contained in mixed deposits of proteins and other materials, so as to disrupt intermolecular bridging within the mixed deposits and weaken the structural integrity of the deposits.

43. A cleaning and disinfecting process according to claim 41, wherein said single solution if surfactant-free.

44. A cleaning and disinfecting process according to any one of claims 41 to 43, wherein the lens is a frequent replacement lens.

45. A cleaning and disinfecting process according to any one of claims 41 to 43, wherein the lens is a Group IV lens.

* * * * *